United States Patent [19]

Sorrenti

[11] Plant 4,834

[45] Mar. 30, 1982

[54] ALMOND TREE

[76] Inventor: Frank Sorrenti, 3127 N. Leonard, Fresno, Calif. 93727

[21] Appl. No.: 119,624

[22] Filed: Feb. 7, 1980

[51] Int. Cl.[3] ..... A01H 5/03
[52] U.S. Cl. ..... Plt./30
[58] Field of Search ..... Plt./30

*Primary Examiner*—Robert E. Bagwill

*Attorney, Agent, or Firm*—Victor Sepulveda

[57] ABSTRACT

Described herein is a new and distinct variety of almond tree which is compared with the Carmel (patented) variety which is characterized by heavy bloom and heavy fruitwood having a relatively longer life span. The fruitwood is denser and with the almonds spread more evenly over the tree providing a higher yield and higher protection.

4 Drawing Figures

ORIGIN OF THE VARIETY

A tree mutation was found in our orchard located in Fresno County, Calif., in the San Joaquin Valley and appears to be closely related to the Carmel almond having many of its characteristics. The new almond tree variety has been recognized for its new and distinctive characteristics which classed is as an almond having a higher production and has a higher density of fruitwood even on its lower branches and does not tend to lose the fruitwood in the lower branches as does the previous varieties.

ASEXUAL REPRODUCTION OF THE VARIETY

Subsequent to origination of the present variety almond tree and recognition of its advantages and characteristics I asexually reproduced such variety by budding it onto a Nemaguard peach tree in an orchard on my ranch in Fresno County, Calif. When grown to maturity and in bearing, such asexual reproduction ran true to the original almond tree in all respects.

SUMMARY OF THE VARIETY

The almond tree of the present variety has the following characteristics:

The fruitwood has proved to be much stronger. The almonds thereon do not tend to cluster but are spread more evenly across the fruitwood, thus giving a higher yield and higher production.

The hull of the fruit has a thin texture and a well sealed shell. The shell is lighter in color and distinguishes the variety from other almonds. It has good blanching quality and a good bleaching quality which lends to it aesthetic value.

DESCRIPTION OF THE DRAWING

The drawing is an illustration by photographic reproduction in color of the leaves, flowers, and the almonds on a branch.

DESCRIPTION OF THE VARIETY

The botanical details of the new distinct variety of almond tree with color definition (except those in common color terms) referenced to Maerz and Paul Dictionary of Color (M&P) are as follows:

Tree:
- *Size.*—Large.

- *Vigor.*—Vigorous.
- *Type growth.*—Spreading.
- *Foliage.*—Dense.
- *Shape.*—Round top.
- *Hardiness.*—Hardy.
- *Production.*—Heavy.
- *Bearing.*—Regular bearer.
- *Distribution of nuts on tree.*—Well and evenly distributed across the fruitwood.

Trunk:
- *Form.*—Stocky.
- *Bark.*—Medium.
- *Texture.*—Medium.
- *Color.*—Light grayish-brown.

Branches:
- *Internodes.*—Medium to short.
- *Branching habit.*—Spreading to medium.
- *Lenticels.*—Numerous, medium to mostly small.
- *Color.*—New wood: Reddish green, some growth was entirely green. Ventral side: Light green. Dorsal side: Brown to brownish green. Mature wood: Reddish-brown to gray, dull. Ventral side: Mostly light green. Dorsal side: Reddish-brown. Older wood: Gray.

Leaves:
- *Amount.*—Abundant.
- *Size.*—Small.
- *Shape.*—Lanceolate.
- *Leaf apex.*—Many acutely pointed, mostly acuminate.
- *Leaf thickness.*—Thin.
- *Texture.*—Smooth.
- *Color.*—Dorsal side: Medium (M&P P/23H7 Mt. Vernon Green). Ventral side: Light green (M&P P/22 G 7 Garland Green). Dorsal side: Dull. Ventral side: Dull.
- *Leaf base.*—Some broadly acute, mostly obtuse.
- *Leaf vein.*—Pinnately net veined.
- *Mid rib.*—Pronounced, medium.
- *Margin.*—Reddish-green, crenate.
- *Leaf.*—Finely crenate to medium crenate. Conformation. — flat.
- *Petiole.*—Long, slender. Color: Dorsal side, M&P P/21 L 7 Parrot Green to P/22 K 3 Box Green with tinge of red at end of petiole. Ventral side, M&P P/10-C-1 Butterfly Green to P/19 K 2, Citron Green.

*Glands.*—Position: Mostly alternate, mixed. Size: Small. Form: Globose. Color: Green. Position on leaf: Mostly on petiole near leaf blade. Stipules: None on current season's growth, none to 2 on older wood.

*Leaf buds.*—Small, pointed.

Flowers:

*Flower buds.*—Amount of bloom: Heavy to very heavy. Period of bloom: Early late, blooms close to the Carmel variety season, full bloom quicker than on the Nonpareil variety (unpatented). First bloom Feb. 28 and in full bloom Mar. 9. Size of blossoms: Large. Color of bloom: White. Flower buds very numerous, many live single fruit buds. Character of fruitwood: Many live fruit and leaf buds with many replacement buds from side or at base of dead stems from previous year. The fruitwood is sturdy and is evenly distributed on the tree.

Crop:

*Tenacity.*—Medium tenacity, easy to harvest.

*Hulling.*—Very easy to hull.

Hull:

*Outer surface.*—Mostly medium to few, smooth to rough.

*Thickness.*—Medium to thin.

*Flesh.*—Medium tough.

*Suture.*—Ridged.

*Color.*—Light green with silvery sheen.

*Dehiscence.*—Opening partially.

*Splitting.*—Along ventral suture, freely at base, in hull, mostly $\frac{1}{3}$ of nut exposed.

Nut:

*Size.*—Mostly medium. Length 29–35 mm average 32.3 mm. Width 13–20 mm average 17.8 mm. Thickness 13–15 mm average 14.4 mm. Weight 0.077 g.

*Form.*—Slightly elongated, ovate to rounded. Thickness, plump. Width to length 17.8/32.3=0.55. Average thickness to width 14.4/17.8=0.80.

*Shell.*—Paper, soft, thin, smooth. Outer shell: Color: M&P P/9 D2 Cream. Crumbling, separates easily. Inner shell: Rough to smooth, medium, mostly well sealed, very few nuts open on ventral side after hulling. Color: Light Straw, M&P P/10 E4 Sunset Yellow. Pits: Small, numerous, deep-many shallow, mostly round. Base: Mostly square to slightly ventrally oblique. Stem scar: Some medium, many small; mostly obtuse. Apex: Acute, many acuminate, broadly curved on ventral side. Wing: Medium to narrow, medium tapered toward base, full at apex of tip. Inner surface: Medium colored (M&P P/11 H7, Inca Gold). Ventral streak: Dark, broad, long, point acute, corky.

Kernel:

*Size.*—Few large, mostly medium to small. Length 21–28 mm average 23.7 mm. Width 11–13 mm average 12.0 mm. Thickness 8–10 mm average 9.2 mm. Weight average 0.0465 oz. per kernel.

*Form.*—Slightly elongated, mostly ovate to rounded, apex pointed, dorsal-ventral edges smoothly curved. Width/length 12.0/23.7=0.506. Thickness/width 9.2/12=0.766.

*Base.*—Mostly square, slightly ventrally oblique, ventrally rounded, dorsally shouldered occasionally.

*Stem scar.*—Some large to mostly medium; obtuse, dark brown.

*Apex.*—Acute to mucronate, tip recurved toward dorsal side mostly.

*Plumpness.*—Slightly wrinkled, slightly furrowed.

*Pellicle.*—Medium to thin, folds on ventral edge mostly near apex half of kernel.

*Pubescence.*—Short to fine, mostly at apex end, rough.

*Color.*—Mostly brown, (M&P P/13 J 11, Sorrell to P/13 L 9, Chipmunk Brown.)

*Defective kernels.*—Gummy: None.

*Flavor.*—Sweet to slightly oily, normal.

*Quality.*—Very good.

*Susceptibility or resistance to insects.*—Good, normal.

*Susceptibility to disease.*—Good, normal susceptibility.

I claim:

1. A new and distinct variety of almond tree substantially as shown and described.

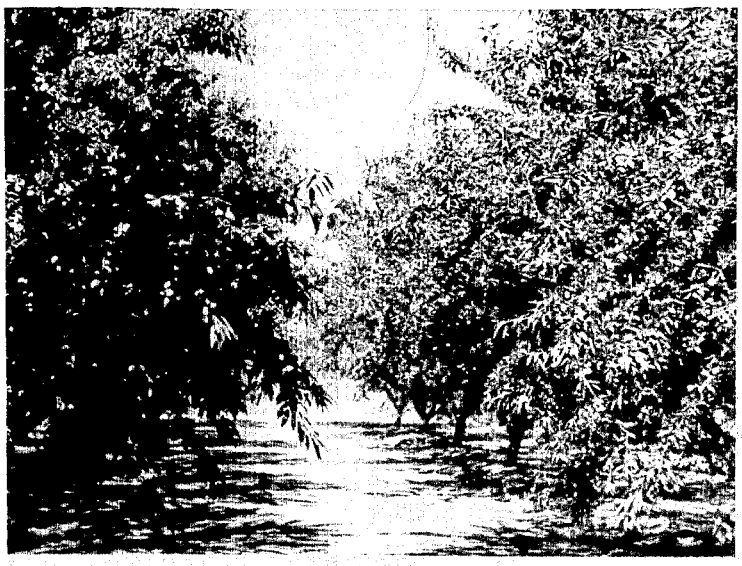
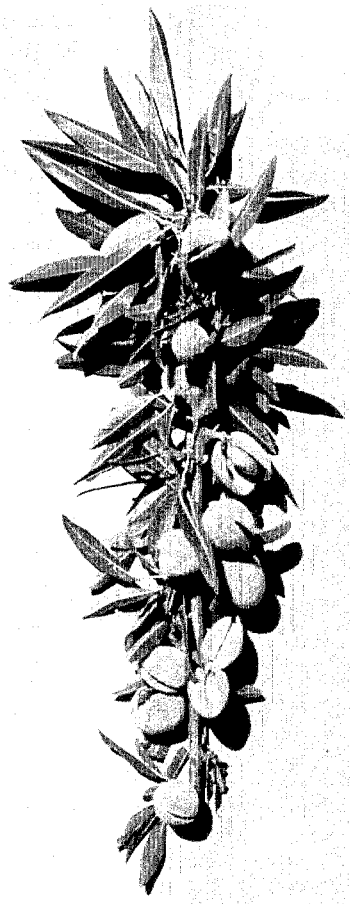
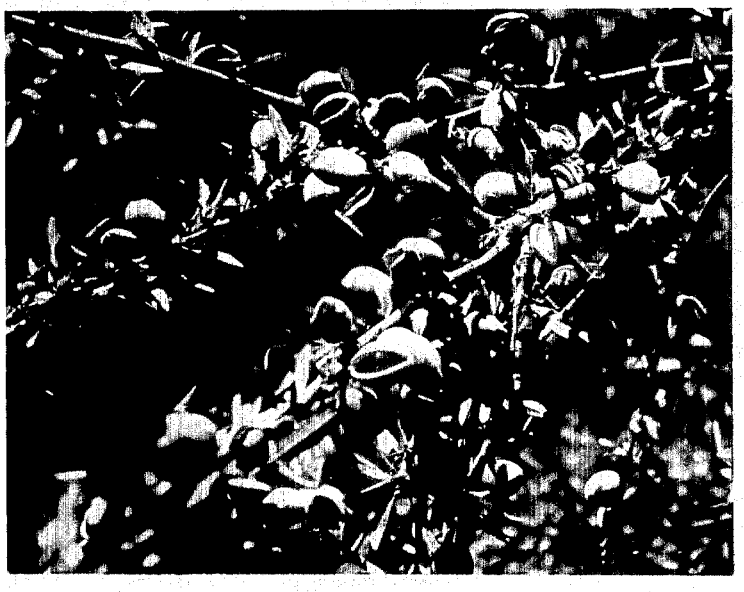
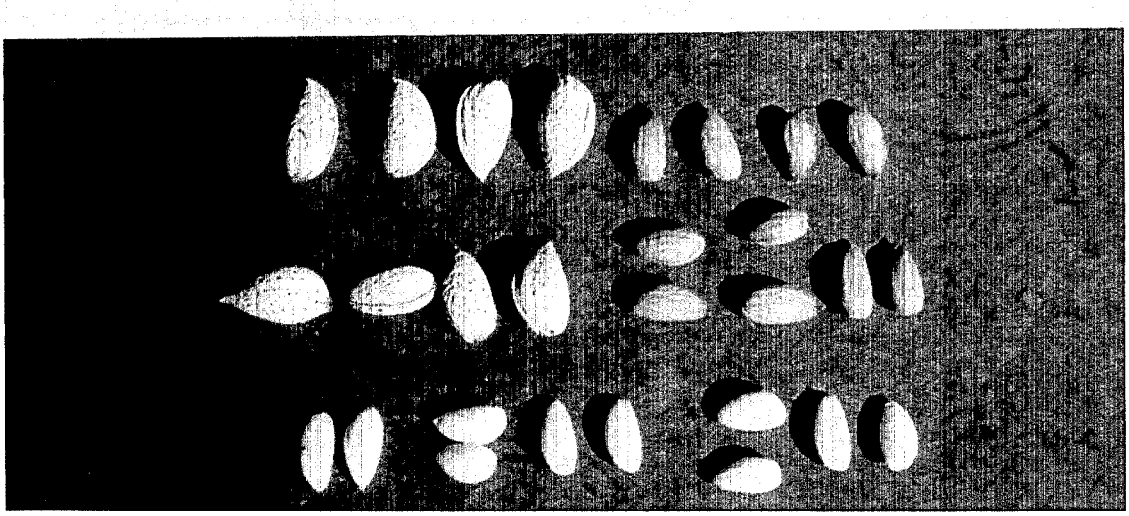

* * * * *